US006248911B1

(12) United States Patent
Canessa et al.

(10) Patent No.: US 6,248,911 B1
(45) **Date of Patent: *Jun. 19, 2001**

(54) PROCESS AND COMPOSITION FOR REFINING OILS USING METAL-SUBSTITUTED SILICA XEROGELS

(75) Inventors: Carlos E. Canessa, East Norriton; Adam J. Brozzetti, West Chester, both of PA (US)

(73) Assignee: PQ Corporation, Berwyn, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/134,445

(22) Filed: Aug. 14, 1998

(51) Int. Cl.[7] .......... C07C 51/47

(52) U.S. Cl. .......... 554/191; 554/174; 554/175; 554/192; 554/196

(58) Field of Search .......... 554/175, 176, 554/191, 192, 196

(56) References Cited

U.S. PATENT DOCUMENTS

| | | | | |
|---|---|---|---|---|
| 1,745,952 | | 2/1930 | Prutzman | 554/191 |
| 1,959,346 | | 5/1934 | Cummins . | |
| 2,475,328 | * | 7/1949 | Lande | 208/289 |
| 2,731,326 | * | 1/1956 | Alexander | 423/338 |
| 3,794,713 | * | 2/1974 | Aboutboul | 423/338 |
| 3,955,004 | | 5/1976 | Strauss et al. | 426/254 |
| 4,093,540 | | 6/1978 | Sen Gupta | 554/80 |
| 4,112,129 | * | 9/1978 | Duensing | 426/417 |
| 4,150,045 | | 4/1979 | Sinha | 554/190 |
| 4,443,379 | | 4/1984 | Taylor et al. . | |
| 4,629,588 | | 12/1986 | Welsh et al. | 554/191 |
| 4,681,768 | * | 7/1987 | Mulfur | 426/417 |
| 4,734,226 | | 3/1988 | Parker et al. | 554/176 |
| 4,735,815 | | 4/1988 | Taylor et al. | 426/417 |
| 4,781,864 | | 11/1988 | Pryor et al. | 554/188 |
| 4,880,574 | | 11/1989 | Welsh | 554/176 |
| 4,880,652 | | 11/1989 | Regutti | 426/417 |
| 4,956,126 | * | 9/1990 | Staal | 554/191 |
| 5,149,553 | | 9/1992 | Berg et al. | 426/330 |
| 5,225,013 | * | 7/1993 | Regutti | 210/778 |
| 5,231,201 | | 7/1993 | Welsh et al. | 554/191 |
| 5,252,762 | | 10/1993 | Denton | 554/196 |
| 5,298,639 | | 3/1994 | Toeneboehn et al. | 544/192 |
| 5,336,794 | * | 8/1994 | Pryor | 554/206 |

FOREIGN PATENT DOCUMENTS

| | | | | |
|---|---|---|---|---|
| 0 376 406 A1 | | 7/1990 | (EP) . | |
| 0 389 057 A2 | | 9/1990 | (EP) . | |
| 0 507 424 A1 | | 10/1992 | (EP) . | |
| 0 558 173 A1 | | 9/1993 | (EP) . | |
| 94/21765 | * | 9/1994 | (WO) | C11B/3/10 |

OTHER PUBLICATIONS

Gutfinger, T. and Letan, A., Pretreatment of Soybean Oil for Physical Refining: Evaluation of Efficiency of Various Adsorbents in Removing Phospholipids and Pigments, *Journal of the American Oil Chemists' Society,* vol. 55, Dec., 1978, pp. 856–859.

* cited by examiner

*Primary Examiner*—Jean F. Vollano
(74) *Attorney, Agent, or Firm*—Ratner & Prestia

(57) ABSTRACT

A process and composition for removing trace contaminants from glyceride oils utilizes a metal-substituted silica xerogel having a pH of at least 7.5 to adsorb at least a portion of the contaminants. The process of the invention includes contacting a glyceride oil with such an adsorbent and then separating the adsorbent from the contaminant-depleted glyceride oil, for example, by filtration. The composition of the present invention includes a metal-substituted silica xerogel having a pH of at least 7.5 and an organic acid blended with the xerogel. Preferably, the organic acid is citric acid. Contaminants which can be removed from glyceride oils during the refinement of such oils by the adsorbent include phospholipids, soaps, detrimental metals, and chlorophyll.

30 Claims, 1 Drawing Sheet

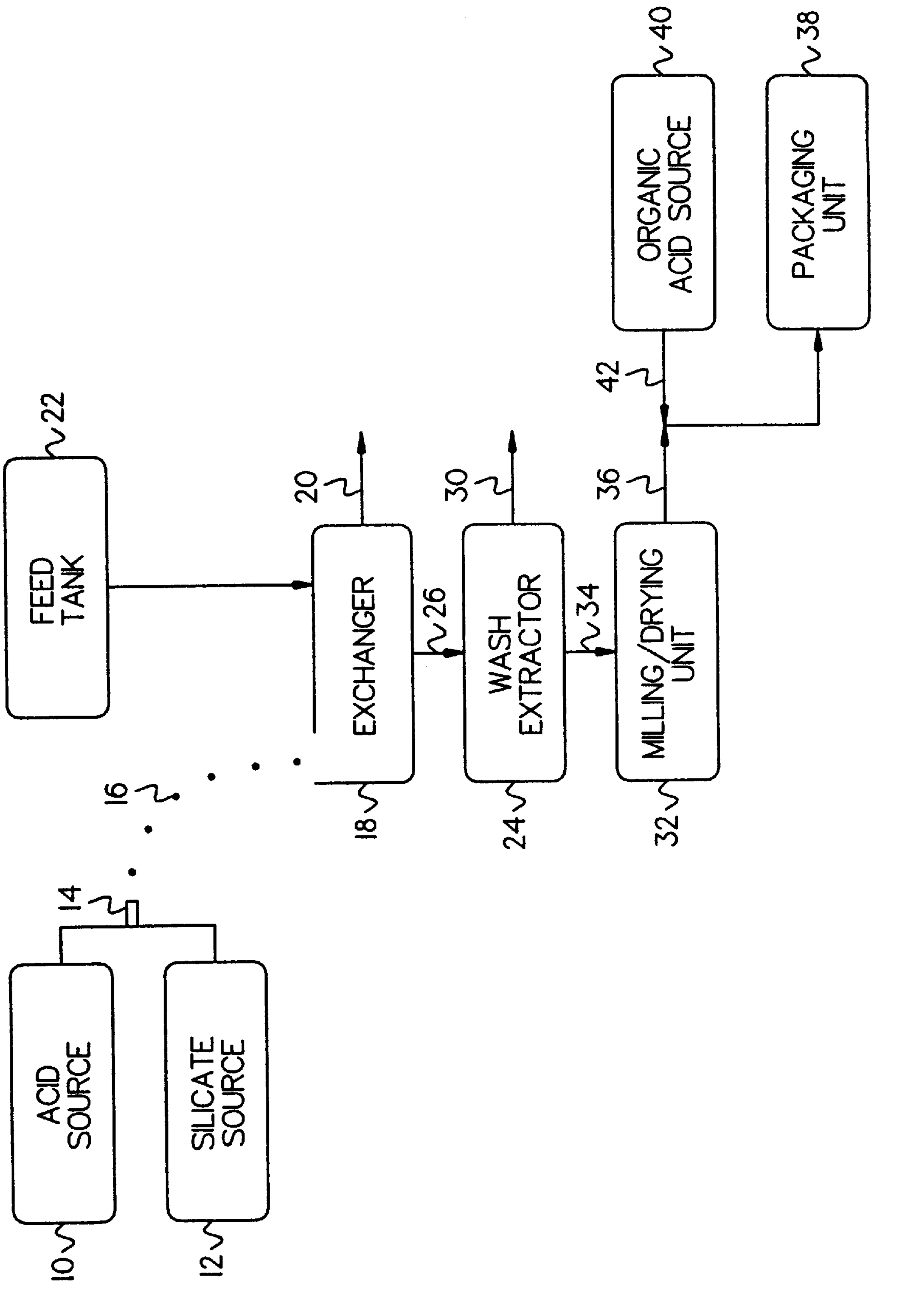
ACID SOURCE
10
SILICATE SOURCE
12
14
16
FEED TANK
22
EXCHANGER
18
20
26
WASH EXTRACTOR
24
30
34
MILLING/DRYING UNIT
32
36
42
ORGANIC ACID SOURCE
40
PACKAGING UNIT
38

PROCESS AND COMPOSITION FOR REFINING OILS USING METAL-SUBSTITUTED SILICA XEROGELS

FIELD OF THE INVENTION

The present invention pertains to the refinement of glyceride oils and particularly to the removal of soaps, phospholipids, detrimental metals, and chlorophyll from such oils.

BACKGROUND OF THE INVENTION

Crude glyceride oils, particularly vegetable oils, are typically refined by a multi-stage process. The first stage of this process typically is degumming by treatment with water or with a chemical such as phosphoric acid, citric acid, or acetic anhydride. Gums (or "phospholipids") include such substances as lecithin and cephalin. About 90% of gums present in crude glyceride oils are capable of being hydrated and therefore are easily removed by a water wash. The remaining 10% can be converted to hydratable forms by the use of phosphoric acid as the degumming agent. Although gums may be separated from the oil at this point or carried into subsequent phases of refining, oil which has been subjected to this degumming step is said to be "degummed" herein. Various chemicals and operating conditions have been used to perform hydration of gums for subsequent separation.

After degumming (or instead of degumming), the oil may be refined by a chemical process including neutralization, bleaching, and deodorizing steps. Alternatively, a physical process may be used, including a pretreating and bleaching step and a steam refining and deodorizing step. Regardless of the particular refining process, it is desirable to reduce the levels of phospholipids, soaps (e.g., sodium oleate), and detrimental metals, all of which can adversely affect colors, odors, and flavors in the finished oil. Such detrimental metals include calcium, iron, and copper, whose ionic forms are thought to be chemically associated with phospholipids (and, possibly, heavy metal soaps) and to negatively affect the quality and stability of the final oil product. It is also desirable to reduce the level of chlorophyll which, if remaining in the oil, can tend to impart an unacceptably high level of green coloring to the oil as well as possibly causing instability of oil upon exposure to light.

Efforts have been made to remove phospholipids, detrimental metal ions, and chlorophyll from oil. For example, U.S. Pat. No. 4,629,588 discloses the use of untreated amorphous silica, and U.S. Pat. No. 4,734,226 discloses the use of an organic acid-treated amorphous silica, as adsorbents of phospholipids and certain metal ions. According to the '226 patent, organic acids, such as citric, acetic, ascorbic, or tartaric acids, are contacted with amorphous silica in a manner which causes at least a portion of the organic acid to be retained within the pores of the silica. According to another patent, namely U.S. Pat. No. 4,781,864, an acid-treated amorphous silica adsorbent is capable of removing both phospholipids and chlorophyll from glyceride oil. According to this patent, a fairly strong acid having a $pK_a$ of about 3.5 or lower is contacted with amorphous silica, and the resulting acid-treated amorphous silica has a pH of 3.0 or lower. The acidic conditions during which the acid-treated amorphous silica is prepared tends to result in the precipitation of metal oxides, especially iron oxide, within the pores of the silica and around the silica particles.

Soaps have been removed from oil in the past by a water wash step of up to 15% (by volume) of the oil being purified. A drawback of this method is that the wash effluent water must be regenerated if it is to be used again in a subsequent stage. Accordingly, it is desirable to utilize an adsorbent which minimizes or eliminates the need for a water wash step for the removal of soap.

It is also desirable to utilize an adsorbent which is capable of reducing the levels of phospholipids, soaps, detrimental metals, and chlorophyll in refining oil. In addition, it is desirable to minimize the amount of adsorbent required, because the adsorbent is eventually separated from the oil before the oil is used. When less adsorbent is used, filtration of the adsorbent is easier and less energy-intensive and tends to minimize oil losses in the filtercake.

SUMMARY OF THE INVENTION

In view of its purposes, the present invention provides a process and composition for removing certain contaminants from glyceride oil. The process of the present invention involves contacting a glyceride oil with an adsorbent comprising a metal-substituted silica xerogel having a pH of at least 7.5 to adsorb at least a portion of the contaminants onto the adsorbent, then separating the adsorbent from the oil. The silica xerogel is metal-substituted in that substantially all of the sodium or potassium ions on and within the silica particles are replaced by certain metal ions, such as magnesium. Even more preferably, the adsorbent also includes an organic acid blended with the metal-substituted silica xerogel prior to the step of contacting the oil with the adsorbent. Even more preferably, the organic acid is citric acid.

The composition of the present invention is an adsorbent comprising a metal-substituted silica xerogel having a pH of at least 7.5 and an organic acid blended with the xerogel. Preferably, the organic acid is citric acid, and the substituting metal is magnesium.

The process and composition of the present invention provide for the removal of certain trace contaminants from glyceride oil during the refinement of the oil. These contaminants include phopholipids, soaps, metal ions, and chlorophyll.

It is to be understood that both the foregoing general description and the following detailed description are exemplary, but not restrictive, of the invention.

BRIEF DESCRIPTION OF THE DRAWING

The invention is best understood from the following detailed description when read in connection with the accompanying drawing. The FIGURE is a schematic view of an embodiment of a process for making a metal-substituted silica xerogel according to the present invention.

DETAILED DESCRIPTION OF THE INVENTION

The present invention is directed to a process and composition for removing trace contaminants from glyceride oils to produce oil products with substantially lowered concentrations of these trace contaminants. As used herein, the term "glyceride oil" is intended to encompass all lipid compositions, including vegetable oils and animal fats and tallows. The term glyceride oil is primarily intended to describe edible oils, namely those oils derived from fruits or seeds of plants and used chiefly in foodstuffs, but it is understood that oils whose end use is as non-edible oils can be purified according to the present invention as well. The process and composition of this invention can also be used to treat fractionated streams derived from these oils.

As used herein, the term "removing" as in "removing trace contaminants from glyceride oils" implies removing at least some percentage of selected contaminants, such as phospholipids, soaps, chlorophyll, and metal ions, but does not necessarily contemplate removing one hundred percent of any of these contaminants. In some cases, however, a trace contaminant may be removed to such an extent that it cannot be detected by known quantitative analysis procedures. The process and composition of the present invention are suitable for use during the refining process of crude oil, namely to remove the particular trace contaminants found in oil yet to be used in a cooking application or other application.

As mentioned above, the trace contaminants which are removed according to the process and composition of the present invention include phospholipids, soaps, chlorophyll, and certain metal ions which are detrimental to the end oil product. The detrimental metal ions removed by the present invention include iron, copper, and phosphorous and, to a lesser extent, sodium and zinc. Soaps removed by the present invention include water-soluble soaps, such as sodium oleate, and, possibly, heavy metal soaps. As shown in the examples below, there is direct evidence that water-soluble soaps (such as sodium oleate) are removed by the present invention and indirect evidence that heavy metal soaps are removed. This indirect evidence is the reduction of certain metals which likely exist, at least to some extent, in the form of heavy metal soaps. Most, and in some cases all, of the phosphorous present is associated with phospholipids; accordingly, the phosphorous content is directly proportional to the phopholipid content in the oil. In addition, it is thought that at least some of the other detrimental metals are also associated with phospholipids. Even without this association, the presence of the metals themselves can adversely affect the taste, odor, and color of the end oil product.

The chlorophyll removed by the present invention refers to all relevant forms of chlorophyll or their degradation products, such as pheophytin. Some glyceride oils contain a relatively high amount of chlorophyll, such as those produced from plants, while others may contain little or no chlorophyll. Either type of oil, however, can be treated and purified according to the present invention and some level of reduction in chlorophyll content can be achieved. The present invention might also remove other contaminants from oil by adsorption, but testing has not been done to confirm the removal of other contaminants.

In its most general form, the adsorbent used in the process of the present invention is a metal-substituted silica xerogel having a pH of at least 7.5. A method of making the metal-substituted silica xerogel of the present invention is discussed in connection with the accompanying FIGURE.

The first step of this process is the partial neutralization of a sodium silicate or potassium silicate solution to form a silica hydrosol. In particular, silica hydrosols are formed by simultaneously and instantaneously mixing aqueous solutions of an acid and sodium or potassium silicate. For example, an acid source 10 may be used to supply an acid, such as sulfuric acid, which is combined with the sodium or potassium silicate solution from silicate solution source 12. The concentrations and flow rates or proportions are adjusted so that the hydrosol contains 8 to 12% $SiO_2$ and so that about sixty to about ninety percent of the alkali metal present in the silicate solution is neutralized. The range over which the alkali metal present in the silicate solution is neutralized is dictated by practical considerations, primarily by the rate of gelation. Thus, a portion of the alkali metal remains with the silica hydrosol as unreacted $Na_2O$ or $K_2O$. The silicate/acid mixture is forced through a nozzle 14. From the nozzle, the mixture forms hydrosol beads 16, which are allowed to set to form a hydrogel, all in a known manner. Such hydrosols gel rapidly and can be allowed to gel in a mass and then be crushed to form particles for further processing. In one embodiment the hydrosol contains about 10% $SiO_2$, has a pH above about 8, and gels in a matter of seconds or less. Such a hydrosol can be formed into spheres by spraying in air.

The hydrogel is then delivered to a bath of a solution of a multivalent metal in exchanger 18. Multivalent metals used to prepare compositions of the present invention are those having ions which can react with the unreacted sodium or potassium ions on the silica surface and within the silica particles in a reversible manner. In other words, the metal ions must be capable of adsorbing or desorbing from silica in response to changes in pH and/or concentration. The metal ions selected also have a greater affinity of adsorption of at least some of the trace contaminants than sodium or potassium, whose ions are replaced by ions of the substituting metal. Preferably, the metal ions of the substituting material have a strong affinity for adsorbing all of the contaminants which are sought to be removed. Also, the metals should preferably not be metals which have been found to be detrimental to the taste, color, or odor of the oil, such as iron, copper, or phosphorous. Among useful metals are magnesium, aluminum, calcium, barium, manganese, and mixtures thereof, with magnesium and aluminum being more preferable and magnesium being the most preferable.

The substituting metal can exist in solution as the ionized form of a metal salt, with a halide, phosphate, nitrate, sulfate, acetate, or oxylate as counter ions to the metal ions in the solution. Preferably, the metal salt is magnesium sulfate. The concentration of the metal ion in the solution should be sufficient to promote reaction (i.e., substitution of the alkali metal ions) of the metal with the silica but not favor precipitation or aggregation of metal species. Typically, the concentration of the metal ions to achieve this function is between about 0.3% to 15% by weight, and preferably between about 3% to 7% by weight. The pH of the metal ion solution is typically about neutral prior to the addition of the hydrogel particles, but increases upon addition of the alkaline hydrogel particles. In one embodiment using a magnesium sulfate solution, the initial pH of the solution is between about 6.9 and 7.2, while the pH of the solution exiting the exchanger is about 8.5.

In exchanger 18, the hydrogel particles are contacted with an aqueous solution of a metal salt, such as magnesium sulfate, for a period of time sufficient to replace the unreacted sodium or potassium on the surface of, and within, the silica particles with the substituting metal. Contact times range depending on the particular conditions and typically vary between fifteen minutes to six hours. The metal-depleted and sodium- or potassium-enriched effluent is withdrawn from exchanger 18 in stream 20. The metal ion bath my be replenished and buffered as needed by metal ion bath feed tank 22. Because the metal in the metal ion solution, such as magnesium, has now replaced the sodium or potassium ions within the silica gel, the hydrogel beads can now be characterized as "metal-substituted, silica hydrogel beads."

These beads are delivered to a wash extractor 24 via stream 26. A feed tank of deionized water is used to remove most or all of the water-soluble salts and any excess acid. Multiple washings may occur with the effluent being withdrawn in line 30 and the washed, metal-substituted silica hydrogel being delivered to a milling/drying unit 32 via line 34. In milling/drying unit 32, the hydrogel is dried at least to the point where its structure no longer changes as a result of shrinkage. All gels having a moisture content at or below that point are termed xerogels. Typically, gels having a moisture content less than about 25% are xerogels. The gels can be dried to anywhere from between about 0.01% to 25% moisture content, preferably between about 8% and about 15%, and most preferably about 12% to form a metal-substituted silica xerogel of the present invention. Milling continues until the average particle size is between about 10 to about 40 microns, although the particular size will depend on the application and other conditions in the oil refinement process. In general, the particles should be in the form of a powder and should not be milled too small such that filtration becomes difficult.

The metal-substituted silica xerogel of the present invention can then be delivered via line 36 to packaging unit 38, where the product is packaged. Alternatively, an organic acid powder can be blended with the metal-substituted silica xerogel prior to packaging. In this embodiment, an organic acid source 40 is used to deliver organic acid powder to line 36 where the organic acid intermixes with the metal-substituted silica xerogel. As used herein, the term "blending" means that the organic acid powder is physically mixed with (but not chemically reacted with), the metal-substituted silica xerogel. The resultant blend is thus merely a physical mixture of two powders, which are chemically inert relative to one another. The organic acid may be any suitable organic acid, and preferably is citric acid, acetic acid, ascorbic acid, tartaric acid, or mixtures thereof, and most preferably is citric acid. An exemplary citric acid is a citric acid anhydride (USP grade) sold by Fisher Chemicals of Pittsburgh, Pa. As with the xerogel particles, the organic acid should be in the form of a powder and not be too small such that filtration becomes difficult. Although not shown, the citric acid may be added to the oil separately from the xerogel, namely without blending with the xerogel before addition to the oil.

Another embodiment of the process to prepare the product of the present invention involves the preparation of a silica gel wherein the hydrosol has a neutral or acidic pH value. According to this embodiment, sufficient or more than sufficient acid is added to neutralize all of the sodium initially present in the silicate. The resulting gel is washed to remove some salts and excess acid. Then, an alkaline solution such as NaOH or KOH is added to the silica gel slurry to provide a pH above about 8, preferably between about 8.3 and about 9, for a time sufficient to allow at least some of the sodium or potassium to become associated with the silica gel. This alkalized or alkaline gel is contacted with a solution of a metal salt, such as magnesium sulfate, for a time sufficient to exchange the sodium or potassium ions associated with the silica gel with magnesium ions.

As mentioned above, the pH of the metal-substituted silica xerogel (without any additives such as an organic acid) is at least about 7.5, and typically at most about 9.5, and preferably between about 8.0 and about 8.5. The pH of the metal-substituted silica xerogel is a function of the pH values of the constituents used to make the xerogel. For example, the pH of the sodium or potassium silicate solutions used to prepare the hydrosols is typically about 12 or 13. The pH of the metal ion solution (also described as the "alkaline solution") must be controlled and may be adjusted during the reaction of the substituting metal with the silica. The agent used to adjust the pH may be any known agent that can achieve and maintain the required pH value in solution while the solution is exposed to silica. Acids, bases, and various buffers can be used as this adjusting agent in a known manner. For most metals, the pH of the alkaline solution should be maintained at a value of between about 7 and about 10.5, and preferably between about 8 to 9.5. Acidic pH values during the substitution of the metal ions tend to cause precipitation of metal oxides in and around the silica particles. Such precipitates tend to be relatively large and tend to block the pores of the silica, thereby reducing efficiency of adsorption. Even after blending with an organic acid, the organic acid and the relative amounts of the two constituents are chosen such that the pH of the adsorbent is above about 7.

The product of the present invention comprises a silica gel reacted with a metal, usually a metal with a valence of two or more. The metal is apparently distributed uniformly from the center of each particle or granule to the surface, and it is not in the form of large metal oxide precipitates either in the pores or around the particles. The amount of metal reacted varies, but should be more than 0.65% wt/wt. The product can contain between about 0.01% to 25% moisture with the balance being $SiO_2$, as shown in Table 1 below:

TABLE 1

| | % by Weight (Wet) |
|---|---|
| Metal | 0.65–15.0 |
| $SiO_2$ | 99.34–94.0 |
| $H_2O$ | 0.01–25.0 |

The most preferred substituting metal ion is magnesium, and preferably 1 to 5% (wet weight) of the xerogel is present as magnesium.

The adsorption step is accomplished by simply contacting the adsorbent of the present invention with the oil, preferably in a manner which facilitates the adsorption, in a conventional manner. The adsorption step may be any convenient batch or continuous process. In any case, agitation or other mixing will enhance the adsorption efficiency of the treated silica.

Adsorption may be conducted at any convenient temperature at which the oil is a liquid. Typically, the oil temperature is between about 80° and 120° C., and is preferably between about 90° to about 110° C. The glyceride oil and metal-substituted silica xerogel are contacted as described above for a period of time sufficient to achieve the desired contaminant percentage reduction in the treated oil. The specific contact time will vary somewhat on the selected process, i.e., batch or continuous; with the condition of the oil to be treated, i.e., degummed or not; with the concentration of the contaminants in the oil; and with the particular adsorbent being used. In addition, the relative quantity of adsorbent brought into contact with the oil will also affect the amount of contaminants removed. The xerogel usage is quantified as the weight percent of amorphous silica (on a dry weight basis after ignition at 1750° F.) divided by the weight of the oil process. The xerogel usage may be from about 0.003% to about 5.0%, preferably less than about 1.0%, and most preferably between about 0.05% to about 0.5%.

The concentration of organic acid, when used, can vary over a wide range depending on the same factors discussed above. The organic acid appears to be particularly suitable in neutralizing soaps and chelating metals. Accordingly, when the unrefined oil contains a large concentration of these two contaminants, then a commensurately larger percentage of organic acid should be used. It has been found that, for some of the glyceride oils tested, organic acid can be added to achieve a concentration of about 10% (by dry weight) to about 30% of the concentration of the xerogel. Preferably, the concentration of organic acid is about 15% to about 20% of the concentration of the xerogel.

Other additives may also be used to adsorb contaminants either added to the oil along with the silica xerogel (or xerogel/organic acid blend) described herein or added separately to the oil. For example, clay is known to adsorb certain chlorophyll pigments found in crude oil. In fact, clay might have a stronger affinity for some chlorophyll pigments than the adsorbent of the present invention. According to a preferred embodiment of the present invention, the oil is heated to a first temperature (e.g., 90° C.,±10° C.); then the silica xerogel (or xerogel/organic acid blend) described herein is added; then the slurry is heated to a second temperature higher than the first (e.g., 10° C.,±10° C.); then clay is added; then the slurry is mixed for a period of time to allow adsorption; and finally the solids are filtered.

Regardless of whether clay is used, the adsorbent (or adsorbents) is separated from the contaminant-depleted glyceride oil in any known manner following adsorption. For example, a filtration device may be used to separate the adsorbent from the contaminant-depleted glyceride oil. The oil may then be subjected to additional finishing processes, such as stream refining, bleaching, and/or deodorizing. The method of the present invention may reduce the phosphorous levels sufficiently to completely eliminate the need for any bleaching steps. Moreover, the reduction of chlorophyll levels achieved with the use of the present invention may also render the bleaching step unnecessary.

EXAMPLES

The following examples are included to more clearly demonstrate the overall nature of the invention. These examples are exemplary, not restrictive, of the invention.

In all of the examples below, the metal-substituted silica xerogel referred to as C930 metal silica xerogel in the, available from PQ Corporation of Valley Forge, Pa., was made according to the following process.

A silica hydrosol containing 12% of $SiO_2$ was prepared by instantaneously mixing solutions of sulfuric acid and sodium silicate. The acid solution had a concentration of 10.5% $H_2SO_4$ and a temperature of about 85° F. The silicate solution had a nominal weight ratio $SiO_2$:$Na_2O$ of 3.2, a solids level of 30.5%, and a temperature of about 85° F. The flow rates of the acid and silicate solutions were adjusted such that 90% of the sodium in the silicate was neutralized; the pH was above about 8. The hydrosol was sprayed into the air and allowed to form into spheres. The gel time was less than one second.

The gelled spheres were introduced into an aqueous solution of magnesium sulfate. The sulfate solution contained about 14% $MgSO_4$ and had a temperature of about 160° F. Sufficient time was allowed for essentially all of the unneutralized sodium to exchange with magnesium. The magnesium substituted silica hydrogel was washed with water until the water-soluble salts were less than 1% by weight. The gel was dried to a loss on drying of about 12% and milled to a median particle size of about 14–15 micrometers. The final product contained about 1.2% Mg, which is stoichiometrically equivalent to the unneutralized sodium in the initially formed gel spheres.

The remaining products referred to in the examples are all commercially available. The L900™ silica hydrogel available from PQ Corporation, the Crosfield XLC silica xerogel, and the Millenium BG-6 silica xerogel are not "metal substituted" as defined herein.

The oil which was treated, in all of the examples below, was soybean oil. In Examples 1–4, the soybean oil, prior to the specific six or four step adsorbent treatments listed below, was first degummed using 3% (by weight) water of the oil to cause most of the gums to settle to the bottom of the oil as sediment. This sediment was separated from the degummed oil by decanting. In Examples 5–8, no degumming was done to the crude oil.

In all of the examples below, the oil was treated with caustic. In particular, the oil was reacted with a 16 Baume sodium hydroxide solution to remove certain fatty acids. By this caustic treatment, soaps are created as by-product. In Examples 1–4, this caustic treatment step was done after the degumming step, while in Examples 5–8, this caustic treatment was done to the crude oil. The term "crude oil" refers to both oil which has not been treated at all and oil which has only been exposed to caustic treatment (but not degummed).

In each of the examples below (other than the rows entitled "Englehard F105 clay"), the treatment process was as follows:

1. Heat oil to 90° C.;
2. Add silica xerogel, with the tables providing the weight of xerogel added in 160 grams of oil;
3. Heatoilto 110° C.;
4. Add 0.6% Englehard F105 clay under 28 mm Hg vacuum;
5. Mix for 20 min;
6. Filter through 10 micron filter paper under air pressure of 20 psi.

In the examples below for the rows entitled "Englehard F105 clay," the treatment process was as follows:

1. Heat oil to 90° C.;
2. Add 0.6% Englehard F105 clay under 28 mm Hg vacuum;
3. Mix for 20 min;
4. Filter through 10 micron filter paper under air pressure of 20 psi.

All measurements of soaps, metals, and color were made following the filtration step using conventional quantitative analysis techniques. Soap was measured as sodium oleate. The tables below show the results of laboratory evaluations of the invention in comparison with other treatments.

Example 1

Crude soybean oil was first degummed then treated with caustic as mentioned above. The resulting degummed soybean oil had a soap content of 332 ppm and metals contents as shown in Table 3. Four samples of this degummed soybean oil were subjected to the six-step treatment process listed above using four different adsorbents in the concentrations listed below in Table 2. Table 2 shows that the metal silica xerogel of the present invention (identified as "C930") performed at least as well as the silica hydrogel even though less material is used on a dry silica basis. It can be seen that metal silica xerogel and the metal silica xerogel with citric acid performed the best in soap removal, with the latter removing soap to below a detectable level. Adding water to the metal silica xerogel with citric acid actually decreased its performance.

TABLE 2

Results of Degummed Soybean Oil Treated with Different Adsorbents Soaps and Dose Percent and Weights

| Adsorbent | % of Oil | % of Oil | Dose Weight Used in 160 g Oil | Soaps (ppm) |
|---|---|---|---|---|
| UNTREATED OIL | As-Is | Dry Silica Wt | | 332 |
| L900 Silica Hydrogel | 0.45 | 0.17 | 0.72 g | 12 |
| C930 Metal Silica Xerogel | 0.15 | 0.13 | 0.24 g | 11 |
| C930 + Citric Acid | 0.15 + 0.03 | 0.13 | 0.24 g + 0.05 g | 0 |
| C930 + Citric Acid + Water | 0.15 + 0.03 + 0.019 | 0.13 | 0.24 g + 0.05 g + 0.03 g | 9 |

Example 2

The same soybean oil of Example 1 was treated as discussed above in the same concentrations with the four different adsorbents in the same manner as in Example 1. Table 3 shows that the metal silica xerogel of the present invention was as effective as the silica hydrogel in removing metals, even though less silica was used on a dry weight basis. Also, when water is added to the xerogel, traces of iron were observed, meaning that the water slightly decreased the activity of the xerogel.

TABLE 3

Results of Degummed Soybean Oil Treated with Different Adsorbents Metals

| Adsorbent | Dry Silica Wt (% of Oil) | Metals (ppm) P | Ca | Cu | Fe | Mg | Mn | K | Na | Zn |
|---|---|---|---|---|---|---|---|---|---|---|
| UNTREATED OIL | | 15.63 | <5.00 | <0.13 | 2.46 | <5.00 | <0.08 | <25.0 | 48.6 | 0.12 |
| L900 Silica Hydrogel | 0.17 | <5.00 | <5.00 | <0.13 | <0.50 | <5.00 | <0.08 | <25.0 | <25.0 | <0.10 |
| C930 Metal Silica Xerogel | 0.13 | <5.00 | <5.00 | <0.13 | <0.50 | <5.00 | <0.08 | <25.0 | <25.0 | <0.10 |
| C930 + Citric Acid | 0.13 | <5.00 | <5.00 | <0.13 | <0.50 | <5.00 | <0.08 | <25.0 | <25.0 | <0.10 |
| C930 + Citric Acid + Water | 0.13 | <5.00 | <5.00 | <0.13 | 0.67 | <5.00 | <0.08 | <25.0 | <25.0 | <0.10 |

Example 3

Two batches of soybean oil were degummed and then treated with caustic as mentioned above in two separate batches to make the oils shown in Table 4. The untreated soap levels were somewhat different for these two batches, with Batch A having 429 ppm soap and Batch B having 574 ppm soap. Accordingly, Table 4 also has a column giving the percent reduction in soaps to facilitate comparisons between the two batches. This table shows that the conventional silica xerogels (i.e., Crosfield XLC and Millenium BG-6), which do not contain the metal functionality, are less effective than silica hydrogel ("L900") in removing soaps from edible oil. The metal-containing silica xerogel of this invention was more effective than silica hydrogel in soap removal even though less was used on a dry silica basis. The performance of the metal-containing silica xerogel is enhanced by the addition of citric acid, which is not true for the Crosfield silica xerogel. While the performance of the Millenium xerogel appears to be almost as good as the metal-containing xerogel, it must be emphasized that the Millenium xerogel has a much higher content of fine particles and filters very poorly compared to all of the other products tested. Some of the apparent soap performance of the Millenium xerogel comes from the tighter filtration of soaps from the oil; this is a significant disadvantage at the plant scale, however, because of slower filtration rates and shorter filter runs.

TABLE 4

Results of Degummed Soybean Oil Treated with Silica Hydrogel and Different Silica Xerogels Soaps and Dose Percent and Weights

| Adsorbent | % of Oil (As-Is) | Dose Weight Used in 160 g Oil | Soaps (ppm) | Soaps (% Removed) |
|---|---|---|---|---|
| UNTREATED OIL Batch A | ♦ — | | 429 | — |
| L900 Silica Hydrogel | 0.45 | 0.72 g | 148 | 65 |
| Crosfield XLC Silica Xerogel | 0.15 | 0.24 g | 219 | 49 |
| Crosfield XLC Silica Xerogel + Citric Acid | 0.15 + 0.03 | 0.24 g + 0.05 g | 282 | 34 |
| UNTREATED OIL Batch B | ♦ — | | 574 | — |
| C930 Metal Silica Xerogel | 0.15 | 0.24 g | 149 | 74 |
| C930 Metal Silica Xerogel + Citric Acid | 0.15 + 0.03 | 0.24 g + 0.05 g | 132 | 77 |

TABLE 4-continued

Results of Degummed Soybean Oil Treated with Silica Hydrogel and Different Silica Xerogels
Soaps and Dose Percent and Weights

| Adsorbent | % of Oil (As-Is) | Dose Weight Used in 160 g Oil | Soaps (ppm) | Soaps (% Removed) |
|---|---|---|---|---|
| Millenium BG-6 Silica Xerogel | 0.16 | 0.24 g | 160 | 72 |
| Engelhard F105 Clay (No silica gel treatment) | 0.60 | 0.96 g | 540 | 6 |

Example 4

Oil samples from Batches A and B of Example 3 were then tested for certain chlorophyll pigments and color bodies as shown below in Table 5. Table 5 shows that the metal-substituted silica xerogel was more effective than conventional silica xerogels and comparable to silica hydrogel in color reduction. Once again, it should be noted that the Millenium xerogel has a higher content of fine particles that will help with the filtration of pigments and color bodies, but adversely affect filtration rates and run lengths in the plant. The addition of citric acid to the metal-containing silica xerogel further improves its color performance.

TABLE 5

Results of Degummed Soybean Oil Treated with Silica Hydrogel and Different Silica Xerogels
Pigments and Color Bodies
(Same Treatment Levels as in Table 3)

| Adsorbent | Pigments (ppm) Chlorophyll a | Chlorophyll b | Beta-Carotene | Color (Lovibond Scale) Red | Yellow |
|---|---|---|---|---|---|
| UNTREATED OIL Batch A | 0.236 | 0 | 10.76 | 1.8 | 70+ |
| L900 Silica Hydrogel | 0.036 | 0 | 2.34 | 0.6 | 9.3 |
| Crosfield XLC Silica Xerogel | 0.075 | 0 | 3.97 | 0.7 | 20 |
| Crosfield XLC Silica Xerogel + Citric Acid | 0.067 | 0 | 3.30 | 0.8 | 15 |
| UNTREATED OIL Batch B | | | | | |
| C930 Metal Silica Xerogel | 0.043 | 0 | 2.31 | 0.6 | 9.0 |
| C930 Metal Silica Xerogel + Citric Acid | 0.020 | 0 | 2.22 | 0.6 | 8.6 |
| Millenium BG-6 Silica Xerogel | 0.053 | 0 | 2.59 | 0.6 | 11.0 |
| Engelhard F105 Clay Only (no silica gel) | 0.066 | 0 | 3.24 | 0.8 | 70+ |

Example 5

The same crude soybean oil was then tested for metals content without any preliminary degumming but with caustic treatment. Table 6 shows results for nine different metals when the non-degummed oil is used. It can be seen that the C930 metal silica xerogel performed the best for phosphorus adsorption, excluding the BG-6 silica xerogel which, as mentioned above, has finer particles giving a tighter filtration and more time for adsorption. Phosphorus is one of the main targets in oil refining because if it is not removed it darkens the oil later in the refining process.

TABLE 6

Results of Crude Soybean Oil Treated with Different Adsorbents (No degumming)
Metals

| Adsorbent | Dry Silica Wt (% of Oil) | Metals (ppm) P | Ca | Cu | Fe | Mg | Mn | K | Na | Zn |
|---|---|---|---|---|---|---|---|---|---|---|
| UNTREATED OIL | | 120 | <34.2 | <0.13 | 7.56 | 19.1 | 0.15 | <25.0 | 183 | 0.59 |
| L900 Silica Hydrogel | 0.17 | 56.9 | 32.5 | <0.13 | 7.34 | 15.6 | 0.14 | <25.0 | 51.4 | 0.51 |
| Crosfield XLC Silica Xerogel | 0.13 | 71.4 | 34.6 | <0.13 | 2.17 | 17.1 | 0.12 | <25.0 | 51.7 | 0.59 |
| Crosfield XLC Silica Xerogel + Citric Acid | 0.13 | 78.8 | 34.3 | <0.13 | 1.55 | 17.1 | 0.12 | <25.0 | 94.6 | 0.64 |
| C930 Metal Silica Xerogel | 0.13 | 43.6 | 27.5 | <0.13 | 12.0 | 13.7 | 0.15 | <25.0 | <25.0 | 0.57 |
| C930 + Citric Acid | 0.13 | 42.0 | 28.2 | <0.13 | 8.8 | 13.8 | 0.14 | <25.0 | 32.2 | 0.58 |

TABLE 6-continued

Results of Crude Soybean Oil Treated with Different Adsorbents (No degumming)
Metals

| Adsorbent | Dry Silica Wt (% of Oil) | Metals (ppm) P | Ca | Cu | Fe | Mg | Mn | K | Na | Zn |
|---|---|---|---|---|---|---|---|---|---|---|
| Millenium BG-6 Silica Xerogel | 0.13 | 40.5 | 25.3 | <0.13 | 4.6 | 12.0 | 0.10 | <25.0 | <25.0 | 0.45 |
| Engelhard F105 Clay Only (no silica gel) | | 88.5 | 36.9 | <0.13 | 5.2 | 16.5 | 0.15 | <25.0 | 110 | 0.56 |

Example 6

The same starting crude soybean oil (i.e., not degummed) was treated with caustic (i.e., sodium hydroxide), to remove free fatty acids, in the same way in two separate batches to make the untreated oils shown in Table 7. As in Example 3, the untreated soap levels were somewhat different for these two batches, with Batch A1 having 441 ppm soap and Batch B having 457 ppm soap. Accordingly, Table 7 also has a column giving the percent reduction in soaps to facilitate comparisons between the two batches. Table 7 shows that the C930 metal silica xerogel again performed the best in soap removal. In both cases the metal silica xerogel with and without citric acid performed the best.

TABLE 7

Results of Crude Soybean Oil Treated with Silica Hydrogel and Different Silica Xerogels (Not Degummed)
Soaps and Dose Percent and Weights

| Adsorbent | % of Oil (As-Is) | Dose Weight Used in 160 g Oil | Soaps (ppm) | Soaps (% Removed) |
|---|---|---|---|---|
| UNTREATED OIL Batch A1 | — | — | 441 | — |
| C930 Metal Silica Hydrogel | 0.15 | 0.24 g | 107 | 76 |
| Millenium BG-6 Silica Xerogel | 0.15 | 0.24 g | 134 | 70 |
| UNTREATED OIL Batch B1 | — | — | 457 | — |
| L900 Silica Xerogel | 0.45 | 0.72 g | 139 | 70 |
| C930 Metal Silica Xerogel | 0.15 | 0.24 g | 122 | 73 |
| C930 Metal Silica Xerogel + Citric Acid | 0.15 + 0.03 | 0.24 g + 0.05 g | 117 | 74 |
| Crosfield XLC Silica Xerogel | 0.15 | 0.24 g | 177 | 61 |
| Crosfield XLC Silica Xerogel + Citric Acid | 0.15 + 0.03 | 0.24 g + 0.05 g | 146 | 72 |
| Engelhard F105 Clay (No silica gel treatment) | 0.60 | 0.96 g | 370 | 19 |

Example 7

The same starting crude soybean oil (i.e., not degummed) was treated with caustic, then tested for soaps. The oil was also treated with a metal-substituted silica xerogel of the present invention as well as a physically similar silica xerogel. This comparative xerogel was prepared in a manner identical to the C930 xerogel of the present invention, except that no magnesium exchange step was done. Accordingly, the comparative xerogel of Table 8 had most characteristics similar to the C930 xerogel of the present invention, such as moisture content, pore volume, pore surface area, pore diameter, and particle size. Table 8 shows that the metal is necessary to achieve good soap removal.

TABLE 8

Results of Crude Soybean Oil Treated with Silica Hydogel and Different Silica Xerogels
Soaps and Dose Percent and Weights

| Adsorbent | % of Oil (As-Is) | Dose Weight Used in 160 g Oil | Soaps (ppm) | Soaps (% Removed) |
|---|---|---|---|---|
| UNTREATED OIL Batch A | — | — | 521 | — |
| C930 Metal Silica Xerogel | 0.15 | 0.24 g | 198 | 62 |
| 0% Magnesium C930 Silica Xerogel | 0.15 | 0.24 g | 327 | 37 |

Example 8

The same starting crude oil (i.e., not degummed) was treated with caustic, then also treated with a metal-substituted silica xerogel of the present invention as well as a physically similar silica xerogel, as described in Example 7. After having been treated by these two adsorbents, the oil was tested for nine different metals. With the exception of zinc, the magnesium-substituted silica xerogel performed better than the 0% magnesium substituted silica xerogel. In general, the magnesium-substituted silica xerogel of the present invention showed much better metal adsorption. In particular, the phosphorous adsorption was reduced by 22% by the silica xerogel of the present invention.

TABLE 9

Results of Crude Soybean Oil Treated with Silica Hydrogel and Different Silica Xerogels Metals

| | Metals (ppm) | | | | | | | | |
|---|---|---|---|---|---|---|---|---|---|
| Adsorbent | P | Ca | Cu | Fe | Mg | Mn | K | Na | Zn |
| UNTREATED OIL | Not tested but same untreated oil for both samples | | | | | | | | |
| C930 Metal Silica Xerogel | 69.9 | 36.3 | <0.13 | 0.63 | 18.2 | 0.11 | <25.0 | 63.5 | 0.55 |
| 0% Magnesium C930 Silica Xerogel | 88.0 | 44.7 | <0.13 | 0.67 | 21.1 | 0.13 | <25.0 | 98.2 | 0.48 |

Although illustrated and described herein with reference to certain specific embodiments and examples, the present invention is nevertheless not intended to be limited to the details shown. Rather, various modifications may be made in the details within the scope and range of equivalents of the claims and without departing from the spirit of the invention.

What is claimed:

1. A process for removing trace contaminants from glyceride oils comprising the steps of:

contacting a glyceride oil with an adsorbent comprising a xerogel having a gel structure comprising silica and a substituting metal occupying a site of said gel structure previously occupied by an unreacted alkali metal, said xerogel having a pH of at least 7.5, to adsorb at least a portion of said contaminants onto said adsorbent thereby leaving a contaminant-depleted glyceride oil, wherein said xerogel is formed by partial neutralization of an alkali metal silicate solution leaving said unreacted alkali metal and replacement of said unreacted alkali metal by said substituting metal, wherein said alkali metal is selected from the group consisting of sodium and potassium and said substituting metal is selected from the group consisting of magnesium, aluminum, calcium, barium, manganese, and mixtures thereof; and separating said adsorbent from said contaminant-depleted glyceride oil.

2. A process in accordance with claim 1, wherein said adsorbent further comprises an organic acid, wherein said acid is blended with said xerogel prior to the step of contacting said glyceride oil with said adsorbent.

3. A process in accordance with claim 2, wherein said organic acid is citric acid.

4. A process in accordance with claim 1, wherein said xerogel has a moisture content of between about 0.01% and about 25%.

5. A process in accordance with claim 1, wherein said substituting metal is magnesium, whereby said xerogel is a magnesium-substituted silica xerogel.

6. A process in accordance with claim 1, wherein said xerogel is made by contacting a silica hydrogel with an alkaline solution containing said substituting metal to form a metal-substituted silica hydrogel and then drying said metal-substituted silica hydrogel sufficiently to form said xerogel.

7. A process in accordance with claim 6, wherein said substituting metal is magnesium and said alkaline solution is a magnesium sulfate aqueous solution.

8. A process in accordance with claim 6, wherein said alkaline solution has a pH of from about 7 to about 10.5.

9. A process in accordance with claim 8, wherein said alkaline solution has a pH of from about 8 to about 9.5.

10. A process in accordance with claim 1, wherein said xerogel is added to said oil in an amount to achieve a concentration of about 0.003% to about 5%, on a dry weight basis.

11. A process in accordance with claim 10, wherein said xerogel is added to said oil in all amount to achieve a concentration of about 0.05% to about 0.5%.

12. A process in accordance with claim 1 further comprising adding an organic acid, separate from said silica xerogel, to said oil.

13. A composition for use in the removal of contaminants from glyceride oil comprising a xerogel having a gel structure comprising silica and a substituting metal occupying a site of said gel structure previously occupied by an unreacted alkali metal, said xerogel having a pH of at least 7.5, and an organic acid blended with said xerogel, wherein said xerogel is formed by partial neutralizaton of an alkali metal silicate solution leaving said unreacted alkali metal and replacement of said unreacted alkali metal by said substituting metal, wherein said alkali metal is selected from the group consisting of sodium and potassium and said substituting metal is selected from the group consisting of magnesium, aluminum, calcium, barium, manganese, and mixtures thereof.

14. A composition in accordance with claim 13, wherein said organic acid is citric acid.

15. A composition in accordance with claim 13, wherein said xerogel has a moisture content of between about 0.01% and about 25%.

16. A composition in accordance with claim 13, wherein said substituting metal is magnesium, whereby said xerogel is a magnesium-substituted silica xerogel.

17. A composition in accordance with claim 13, wherein said xerogel is made by contacting a silica hydrogel with an alkaline solution containing said substituting metal to form a metal-substituted silica hydrogel and then drying said metal-substituted silica hydrogel sufficiently to form said xerogel.

18. A composition in accordance with claim 17, wherein said substituting metal is magnesium and said alkaline solution is a magnesium sulfate aqueous solution.

19. A composition in accordance with claim 17, wherein said alkaline solution has a pH of from about 7 to about 10.5.

20. A composition in accordance with claim 19, wherein said alkaline solution has a pH of from about 8 to about 9.5.

21. A process in accordance with claim 1, wherein said substituting metal is selected from the group consisting of magnesium, aluminum, calcium, and mixtures thereof.

22. A composition in accordance with claim 13, wherein said substituting metal is selected from the group consisting of magnesium, aluminum, calcium, and mixtures thereof.

23. A process for removing phospholipids, soaps, metal ions, and chlorophyll from glyceride oils comprising the steps of:

contacting a glyceride oil with an adsorbent comprising a xerogel having a gel structure comprising silica and a substituting metal occupying a site of said gel structure previously occupied by an unreacted alkali metal, said xerogel having a pH of at least 7.5, to adsorb at least a portion of said phospholipids, soaps, metal ions, and chlorophyll onto said adsorbent thereby leaving a contaminant-depleted glyceride oil, wherein said xerogel is formed by partial neutralization of an alkali metal silicate solution leaving said unreacted alkali metal and replacement of said unreacted alkali metal by said substituting metal, wherein said alkali metal is selected from the group consisting of sodium and potassium and said substituting metal is selected from the group consisting of magnesium, aluminum, calcium, is barium, manganese, and mixtures thereof; and separating said adsorbent from said contaminant-depleted glyceride oil.

24. A process in accordance with claim 23, wherein said adsorbent further comprises an organic acid, wherein said acid is blended with said xerogel prior to the step of contacting said glyceride oil with said adsorbent.

25. A process in accordance with claim 23, wherein said organic acid is citric acid.

26. A process in accordance with claim 23, wherein said substituting metal of said xerogel is magnesium, whereby said xerogel is a magnesium-substituted silica xerogel.

27. A process in accordance with claim 23, wherein said substituting metal is selected from the group consisting of magnesium, aluminum, calcium, and mixtures thereof.

28. A process for removing phospholipids, soaps, metal ions, and chlorophyll from glyceride oils comprising the steps of:

heating a glyceride oil to a first temperature;

adding a first adsorbent comprising a xerogel having a gel structure comprising silica and a substituting metal occupying a site of said structure previously occupied by a unreacted alkali metal, said xerogel having a pH of at least 7.5, to said glyceride oil to form a first slurry, wherein said xerogel is formed by partial neutralization of an alkali metal silicate solution leaving said unreacted alkali metal and replacement of said unreacted alkali metal by said substituting metal, wherein said alkali metal is selected from the group consisting of sodium and potassium and said substituting metal is selected from the group consisting of magnesium, aluminum, calcium, barium, manganese, and mixtures thereof;

heating said first slurry to a second temperature higher than said first temperature;

adding a second adsorbent comprising clay to said first slurry to form a second slurry;

mixing said second slurry for a period of time to allow adsorption of at least a portion of said phospholipids, soaps, metal ions, and chlorophyll onto said first adsorbent and said second adsorbent thereby leaving a contaminant-depleted glyceride oil; and separating said first adsorbent and said second adsorbent from said contaminant-depleted glyceride oil.

29. A process in accordance with claim 28, wherein said first temperature is between about 80° C. to 100° C. and said second temperature is between about 100° C. to 120° C.

30. A process in accordance with claim 28, wherein said substituting metal is selected from the group consisting of magnesium, aluminum, calcium, and mixtures thereof.

* * * * *

UNITED STATES PATENT AND TRADEMARK OFFICE

CERTIFICATE OF CORRECTION

PATENT NO. : 6,248,911 B1
DATED : June 19, 2001
INVENTOR(S) : Carlos E. Canessa et al.

It is certified that error appears in the above-identified patent and that said Letters Patent is hereby corrected as shown below:

Column 16, claim 11,
Line 29, delete "all", and insert therefore -- an --.

Column 17, claim 25,
Line 32, delete "23", and insert therefore -- 24 --.

Signed and Sealed this

Nineteenth Day of February, 2002

*Attest:*

JAMES E. ROGAN

*Attesting Officer*

*Director of the United States Patent and Trademark Office*

UNITED STATES PATENT AND TRADEMARK OFFICE

CERTIFICATE OF CORRECTION

PATENT NO. : 6,248,911 B1
DATED : June 19, 2001
INVENTOR(S) : Carlos E. Canessa et al.

It is certified that error appears in the above-identified patent and that said Letters Patent is hereby corrected as shown below:

Column 16,
Line 29, delete "all", and insert therefore -- an --.

Column 17,
Line 32, delete "23", and insert therefore -- 24 --.

Signed and Sealed this

Sixteenth Day of July, 2002

*Attest:*

JAMES E. ROGAN

*Attesting Officer* *Director of the United States Patent and Trademark Office*